United States Patent [19]

March et al.

[11] 4,430,263

[45] Feb. 7, 1984

[54] HAPTEN-INHIBITOR IMMUNOASSAY

[75] Inventors: Steven C. March, Libertyville; John W. Safford, Jr., Wauconda; Susan E. Magic, Lake Bluff, all of Ill.

[73] Assignee: Abbott Laboratories, North Chicago, Ill.

[21] Appl. No.: 114,021

[22] Filed: Jan. 21, 1980

Related U.S. Application Data

[63] Continuation of Ser. No. 943,073, Sep. 18, 1978, abandoned.

[51] Int. Cl.³ .................. G01N 31/54; C12N 9/99; C07G 7/00
[52] U.S. Cl. .................. 260/112 R; 435/7; 435/184; 260/112 T; 436/500
[58] Field of Search .................. 435/7, 184; 260/112.5 R, 112 R, 121

[56] References Cited

U.S. PATENT DOCUMENTS

| | | | |
|---|---|---|---|
| 3,049,530 | 8/1962 | Rackis et al. | 435/184 |
| 3,912,704 | 10/1975 | Singh | 435/184 |
| 3,957,342 | 8/1976 | Gross | 260/112 R |
| 3,983,099 | 9/1976 | Niswender | 260/112.5 R |
| 4,043,872 | 8/1977 | Blakemore et al. | 435/7 |
| 4,065,354 | 12/1977 | Ullman et al. | 435/7 |
| 4,130,462 | 12/1978 | Rubenstein et al. | 435/7 |
| 4,134,792 | 11/1979 | Boguslaski et al. | 435/7 |

OTHER PUBLICATIONS

Derwent, "Natural Products," p. 33 Week A26, Mile-46105A/26 DT2754-26.
Schroeder, et al., "Specific Binding Reactions Monitored with Ligand-Cofactor Conjugates and Bacterial Luciferase", *Anal. Biochem.*, vol. 72 (1976), pp. 283-392.
Carrico, et al., "A Method for Monitoring Specific Binding Reactions with Cofactor Labeled Ligands", *Anal. Biochem.*, vol. 72 (1976), pp. 271-282.

*Primary Examiner*—Thomas G. Wiseman
*Attorney, Agent, or Firm*—J. J. McDonnell; D. K. Shelton

[57] ABSTRACT

A specific binding assay method employing, as a labeling substance, a reversible trypsin inhibitor for the detection of a hapten. Competition between the hapten to be determined and hapten trysin inhibitor conjugate for antibody to the hapten, in the presence of enzyme, followed by addition of enzyme substrate provides an effective method for hapten analysis. The preferred trypsin inhibitor is a protein having a molecular weight range of 2,000-75,000. The preferred ratio of the hapten to the inhibitor in the conjugate is between 1:1 and 3:1.

2 Claims, No Drawings

HAPTEN-INHIBITOR IMMUNOASSAY

This is a continuation, of application Ser. No. 943,073, filed Sept. 18, 1978, now abandon.

BRIEF DESCRIPTION OF THE INVENTION

The present invention encompasses an immunoassay method for determining hapten in a test sample comprising:
(a) intermixing with an aqueous solution of the test sample substantially free of interfering protein;
  (i) hapten-enzyme inhibitor conjugate,
  (ii) antibody to the hapten, said antibody inactivating the enzyme inhibitor when bound to the hapten-enzyme inhibitor conjugate,
  (iii) enzyme reversibly inhibited by hapten-enzyme inhibitor conjugate,
(b) adding substrate to the enzyme, and monitoring the enzyme substrate reaction.

The present invention also includes novel reagents; hapten-enzyme inhibitor-conjugates, useful for practicing the above process.

BACKGROUND OF THE INVENTION

A variety of enzyme immunoassay techniques are known. These include methods where an enzyme is bound to an antibody or antigen to be detected. Competition between the enzyme labeled species and unknown for the binding partner bound to a solid support is measured. The enzyme remaining in the solution is measured by reaction to substrate.

Homogeneous enzyme immunoassay techniques are described in U.S. Pat. Nos. 4,043,872 (hapten bound to enzyme) and 4,065,354 (hapten bound to lysozyme). Enzyme cofactor labeled ligands are described (Analytical Biochemistry 72, 271 (1976) and ibid 283).

The present invention is particularly distinct in that it involves conjugation of the hapten to be determined to a protein (m.w. 2,000 to 75,000) which is a reversible enzyme inhibitor. Competition between the hapten to be determined and hapten enzyme inhibitor conjugate for antibody to the hapten, in the presence of enzyme, followed by addition of enzyme substrate provides an effective method for hapten analysis.

Colorimetric change is conveniently measured on a bichromatic spectrophotometer of the type described in U.S. Pat. Nos. 3,748,044; 3,831,618; 3,833,304; 3,900,289; 3,817,424; and 3,811,780 (hereinafter referred to as bichromatic analyzer).

DETAILED DESCRIPTION OF THE INVENTION

The present invention involves a method for determining hapten in test samples such as biological fluids and involves the use of novel reagents which are hapten-enzyme inhibitor conjugates.

Haptens are protein free bodies, generally of low molecular weight that do not induce antibody formation when injected into an animal, but are reactive to antibodies. Antibodies to hapten are raised by first conjugating the hapten to a protein and injecting the conjugate product into an animal or human. the resulting antibodies are isolated by conventional antibody isolation techniques. For purposes of the present invention, the antibodies should be substantially free of serum protein inhibitors such as indicator enzymes used in the test or inhibitors to antibody binding. These are conveniently removed by ion exchange chromatography on an anion exchange column or other suitable protein separation technique.

Representative haptens determinable by methods of the present invention are steroids such as estrone, estradiol, cortisol testosterone, progesterone, chenodeoxycholic acid, digoxin, cholic acid, deoxycholic acid, lithocholic acids and the ester and amide derivatives thereof; vitamins such as vitamin B-12, folic acid; thyroxine, triiodothyronine, histamine, serotonin, prostaglandins such as PGE, PGF, PGA, adrenalin, noradrenalin and drugs such as opiates, theophylline, dilantin, aminoglycoside antibiotics like gentimycin, tobramycin.

Enzyme inhibitors and their enzyme compliments useful for practicing the present invention are:

| INHIBITOR-ENZYME COMPLIMENT | |
|---|---|
| Inhibitor | Enzyme |
| Soybean Trypsin Inhibitor (STI) | Trypsin (3.4.21.4) Plasmin (3.4.31.7) |
| mw ≈ 21,000, commercially available | |
| Pancreatic Trypsin Inhibitor (P.T.I.) | Trypsin Kallikrein Chymotrypsin (3.4.21.1) Plasmin |
| mw ≈ 6,000, commercially available, also known as aprotinin | |
| Legume Inhibitors | |
| (lima bean, jack bean, potato, pea, etc.) commercially available | Trypsin Chymotrypsin |
| Avian Ovomucoid | |
| (chicken, turkey, duck, quail, etc.) commercially available | Trypsin Chymotrypsin |
| Duck Ovomucoid | |
| (3rd domain) enzyme isolated from pronase (myxobacter) | $\alpha_1$ Lytic Protease |
| Serum Inhibitors | |
| Antithrombin III | Thrombin |
| mw ≈ 65,000 | |
| $\alpha_1$ Protease Inhibitor ($\alpha_1$ Antitrypsin) | Trypsin Elastase (3.4.31.11) Chymotrypsin Thrombin |
| mw ≈ 54,000, commercially available | |
| Arginal Inhibitors | |
| Leupeptin | Trypsin |
| Antipain | Trypsin, Papain |
| Pepstatin | Pepsin (3.4.23.1), acid proteases |
| Chymostatin | Chymotrypsin, Papain (3.4.22.2) |

Proteinase inhibitors of microbial origin. Structure is small polypeptide with aldehyde instead of carboxylic acid at C terminal arginine. Reference: H. Umezawa, "Enzyme Inhibitor of Microbial Origin", see also II.

| Snake Venom Proteinase Inhibitors | |
|---|---|
| Russell's Viper Inhibitor II | Trypsin Kallikrein Plasmin Chymotrypsin | mw ≈ 6,900; Ki > $10^{-9}$; Ref. Takahashi, see Ref. II

| C.P.I. Potato Inhibitor | Carboxypeptidase A (3.4.12.2) Carboxypeptidase B (3.4.12.3) |
|---|---| mw ≈ 3,000; Ki 5 × $10^{-8}$; non-serine protease; C. A. Ryan, see Ref. II

| Placental RNAse Inhibitor | Ribonuclease (3.1.4.22) |
|---|---| mw ≈ 50,000; Ki ≈ 3 × $10^{-10}$M; non-serine protease; references:
(1) P. Blackburn, G. Wilson, and S. Moore, J. Biol. Chem., 252:5909 (1977);

| INHIBITOR-ENZYME COMPLIMENT | |
|---|---|
| Inhibitor | Enzyme |
| (2) S. Moore, J. Chromatog. 159, 3–12 (1978) | |

Notes
(1) General reviews or references:
I. Bayer Symposium V on Proteinase Inhibitors; H. Fritz, H. Tschesche, L. J. Green, and E. Truschirt, editors, Springer-Verlag, 1974.
II. Proceedings of the Int'l Research Conference on Proteinase Inhibitors, H. Fritz and H. Tschesche, editors, Walter de Gruyter, 1971.
III. M. Laskowski, Jr. and R. W. Sealock, "Protein Proteinase Inhibitors", Chapter 11, in The Enzymes The inhibitors useful in practicing the present invention are protein molecules having a molecular weight of about 2,000 to 75,000 and act as reversible enzyme inhibitors. Haptens are bound to the inhibitor protein by well known chemical techniques. More commonly an amino or carboxyl function on a protein is reacted with amino, carboxy, hydroxy functional group on a hapten to form an ester or amide bond. Glutaraldehyde in the presence of a carbodiimide links an amine containing hapten with inhibitor protein by condensing with the amino moiety of each. Example I illustrates the reaction of an activated ester of thyroxine with an inhibitor protein. The hapten can be functionalized with haloacetyl and reacted with the inhibitor to provide a hapten-inhibitor conjugate. For example, N-bromoacetyl-L-thyroxine methyl ester is reacted with soybean trypsin inhibitor to form a suitable hapten-inhibitor conjugate. Thus, common methods for binding small molecules to proteins are used to provide enzyme-inhibitor conjugates of the present invention. The same techniques used to link haptens to proteins for the purpose of preparing antibodies to the haptens are also useful for binding the hapten to an enzyme inhibitor. Therefore, haptens to which antibodies have been raised by conjugation to proteins are analyzed by methods of the present invention and preparing hapten-inhibitor conjugated reagents of the present invention.

It is desirable to have 1, 2 or 3 hapten molecules per molecule of inhibitor. Conjugates having larger numbers of hapten molecules bound to the inhibitor proteins are operable but less desirable.

Particularly preferred enzyme-inhibitor conjugates are: soybean trypsin inhibitor having thyroxine, triiodothyronine, conjugated thereto. Thus, thyroxine derivatives of the formula

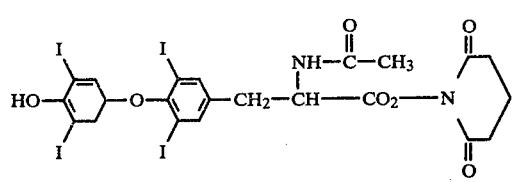

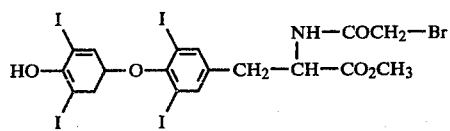

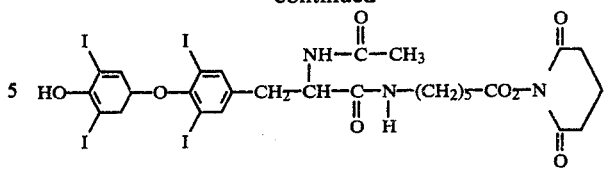

are reacted with trypsin inhibitor to provide a hapten-trypsin inhibitor conjugate having 1–3 molecules of thyroxine bound thereto.

Analytical substrates for proteolytic enzymes such as trypsin, plasmin, and thrombin are well known and include compounds such as α-N-L-arginine-2-naphthylamide and other di, tri and higher order arginine and lysine peptides with chromogenic amide leaving groups, Arch. Bioch. Bioph. 96, (1961) 271; Thrombosis Res. 1, (1972) 267; U.S. Pat. No. 3,884,896 and J. Biol. Chem. 250, (1975) 7366. The colored products are measured by spectrophotometric techniques.

Thyroxine concentrations $10^{-9}$ to $10^{-7}$ molar are conveniently detected using thyroxine-trypsin inhibitor conjugate $10^{-9}$ to $10^{-6}$ molar; trypsin $10^{-9}$ to $10^{-6}$ molar; antibody to thyroxine $10^{-9}$ to $10^{-7}$ molar, and trypsin substrate concentration in large excess, about $10^{-4}$ molar.

Thyroxine containing sample (e.g., serum) is pretreated to inactivate or remove interfering protein. Interfering protein can be removed by organic solvent precipitation with ethanol, methanol, etc. Heat treatment at basic pH is effective for inactivating protein in the test sample. Those skilled in the art will recognize a wide variety of methods for removing interfering protein. In this way, the test sample is rendered substantially free of interfering protein.

EXAMPLE I

A. N-acetyl Thyroxine

Thyroxine sodium salt, pentahydrate, (6.0 g, $6.7 \times 10^{-3}$ mole) is dissolved with stirring in 60 ml of ethanol to which 60 ml of 2 N ammonium hydroxide is added. The solution is gravity filtered into 120 ml of cold 5% hydrochloric acid (HCl). The free acid is formed immediately and is precipitated from solution. The creamy white product is collected, washed thoroughly with water and dried overnight (37° C., 1 mm pressure) to yield 4.99 g of solid.

The solid is transferred to a 500 ml flask and treated with 100 ml of dimethyl formamide (DMF) and 60 ml of acetic anhydride with stirring for one hour. The solution is then titrated with water, usually a volume equal to the starting volume of 160 ml, until the precipitate does not disappear when swirled. The suspension is cooled at 4° C. overnight to obtain a solid collected by suction filtration.

The acetylated solid is dissolved in 120 ml of ethanol to which 25 ml of 1 N sodium hydroxide is added. The reaction is allowed to proceed for one hour with stirring to hydrolyze any O-acetyl product present. The N-acetylated product is precipitated with 300 ml cold 5% HCl, collected by suction filtration and dried to provide N-acetyl thyroxine (3.35 g).

B. N-hydroxysuccinimide ester of N-acetyl throxine

To a reaction vessel equipped with stirrer and teflon lined cap are added 3.35 g N-acetyl thyroxine ($4.09 \times 10^{-3}$ mole), 6.7 ml dry dimethyl formamide (DMF), 6.7 ml dry tetrahydrofuran (THF), 496 mg of N-hydroxysuccinimide ($4.3 \times 10^{-3}$ mole), and 884 mg of dicyclohexylcarbodiimide ($4.3 \times 10^{-3}$ mole). The reaction mixture is stirred at room temperature for 3–4 hours, and the appearance of a precipitate, dicyclohexylurea, noted. The precipitate is filtered off and washed with a small amount of tetrahydrofuran (THF). The THF is removed in vacuo on a rotary-evaporator. The product is separated from the remaining DMF by oiling out the active ester with approximately 20 ml of ether hexane mixture (95:5). The organic layer is decanted and the trituration procedure is repeated two additional times using ether. The oil is bubbled under high vacuum and scratched until a glassy solid is obtained. The solid is transferred to a dessicated container and stored at 4° C.

C. Conjugation of N-hydroxysuccinimide ester of N-acetyl thyroxine with soybean trypsin inhibitor Soybean trypsin inhibitor (STI) (Sigma Chemical) is chromatographed on Sephadex G-75 prior to all conjugation experiments. The recovered STI is dialyzed to remove any traces of amino reactive buffer salts and then lyophilized for storage.

STI is dissolved in 50 ml of borate-saline buffer pH 8.5, to a concentration of 16 mg/ml (38 μmole). N-hydroxysuccinimide ester of N-acetyl thyroxine (378 μmole, 346 mg) is dissolved in 50 ml of DMF in a separate container. Aliquots (2 ml) of the active ester in DMF are added to the STI at 5 minute intervals until all the active ester has been added. The reaction mixture is stirred at room temperature for an additional 3.5 hours, then terminated by dialysis against 2 liters of aqueous triethylamine pH 11. Chromatography of the product on a Sephadex G-75 column ($5 \times 100$ cm) equilibrated with aqueous triethylamine, pH 11 is then conducted to isolate thyroxine ($T_4$) conjugated to soybean trypsin inhibitor from free $T_4$. Fractions containing 1–2 molecules of thyroxine per molecule of protein are isolated as the preferred reagent. Higher substituted fractions were obtained, although operable, they were less preferable.

D. Coupling of N-acetyl thyroxine mixed anhydride to STI

N-acetyl thyroxine (246 mg, 0.3 mMole) is dried well and dissolved in 10 ml of dry dimethylformamide (DMF). The solution is cooled to 4° C. and 40 μl of triethylamine (0.3 mMole) are added. With vigorous stirring, 0.3 mMole (130 mg) of isobutyl chloroformate was added. After the mixed anhydride is incubated 15 minutes at 4° C, the preparation was added to 10 ml of STI (100 mg, 4.65 μmole) in 0.05 M sodium phosphate buffer, pH 9.5. The conjugation mixture (50% DMF—50% water) becomes cloudy and is stirred overnight at 4° C. The product is dialyzed against phosphate buffer pH 7.0, lyophilized, and active inhibitor fractions isolated by chromatography on Sephadex G-75. Fractions with high substitution of $T_4$ (approximately 11 mole. ratio of $T_4$ to STI) do not contain active inhibitor. Fractions which contain approximately 1–2 moles of $T_4$ bound per mole of STI are active in the trypsin inhibition and antibody modulation tests.

EXAMPLE II

Antibody Modulation vs. Thyroxine—Soybean Trypsin Inhibitor Dilution

A working solution of 2.0 mg/ml gamma globulin (chromatographically isolated from sheep $T_4$ antibody) is prepared in 0.1 M HEPES (N-2-hydroxyethylpiperazine-N'-2-ethanesulfonic acid) buffer, pH 8.0, containing 0.1% gelatin. A stock solution of the STI-$T_4$ (soybean trypsin inhibitor-thyroxine) conjugate ($8 \times 10^{-7}$ M) is also prepared in HEPES-gelatin buffer, pH 8.0. A trypsin stock solution is made at $1 \times 10^{-7}$ M in dilute HCl, pH 3.0, and stored at 4° C. The trypsin working reagent is diluted to a concentration of $8.2 \times 10^{-8}$ M with HCl gelatin, pH 3.0. Equal volumes (50 μl) of the thyroxine STI conjugate and antibody are mixed and incubated at room temperature for 5 minutes. Trypsin is then added to the mixture, incubated for 30 seconds, and a 25 μl portion of the assay mixture diluted into a cuvette with 250 μl of substrate (0.5 mM benzoylphenylalanylvalyl arginine p-nitroaniline in 0.05 M Tris pH 8.1 with 0.01 M $CaCl_2$). The change in absorbance with time (t=5.5 minutes less t=0.5 minutes) is recorded using a Bichromatic Analyzer equipped with a 380/450 mμ filter. The following table gives the results for a suitable conjugate prepared in Example I.

TABLE I

| STI-$T_4$ Concentration (Molar) | Antibody Modulation of STI-$T_4$ | | | Percent[3] Modulation |
|---|---|---|---|---|
| | Observed Activity (Absorbance)[1] | | | |
| | STI-$T_4$ | STI-$T_4$ + Ab[2] | Difference | |
| $2.08 \times 10^{-8}$ | 0.573 | 0.652 | 0.078 | 76 |
| $4.17 \times 10^{-8}$ | 0.492 | 0.632 | 0.140 | 76 |
| $8.33 \times 10^{-8}$ | 0.323 | 0.583 | 0.260 | 74 |
| $1.67 \times 10^{-7}$ | 0.157 | 0.482 | 0.325 | 63 |
| $3.33 \times 10^{-7}$ | 0.088 | 0.300 | 0.212 | 36 |
| $6.67 \times 10^{-7}$ | 0.074 | 0.135 | 0.061 | 10 |
| $1.33 \times 10^{-6}$ | 0.055 | 0.071 | 0.016 | 2.5 |

[1] Activity of trypsin control (without STI-$T_4$) is 0.675.
[2] Approximately $7.4 \times 10^{-8}$M antibody (Ab) binding sites, K ≈ $1.3 \times 10^9$
[3] Percent modulation calculated from the observed activity $$\frac{\text{(Activity in presence of Ab + STI-}T_4\text{)} - \text{(Activity in presence of STI-}T_4\text{)}}{\text{(Activity of enzyme)} - \text{(Activity in presence of STI-}T_4\text{)}} \times 100$$

EXAMPLE III

Antibody Modulation of Thyroxine—Soybean Trypsin Inhibitor (Antibody Dose Response Curve)

Increasing concentrations of $T_4$ antibody (IgG fraction as in Example II) are added to a series of tubes containing constant STI-$T_4$ ($17 \times 10^{-8}$ M). The reagents are allowed to react for 5 minutes at room temperature before trypsin is added. The assay procedure described in the first series of experiments (Table I) is followed. The modulation obtained is presented in Table II.

TABLE II

| Antibody Dose Response Curve | | | |
|---|---|---|---|
| Conc of $T_4$ (mg/ml) Antibody in Incubation Mixture[2] | Observed Activity (Absorbance) | Increase due to Antibody | Percent Modulation[3] |
| 8.3 | 0.664 | 0.450 | 45 |
| 4.15 | 0.700 | 0.486 | 49 |
| 2.08 | 0.686 | 0.472 | 47 |
| 1.04 | 0.393 | 0.179 | 18 |
| 0.52 | 0.270 | 0.056 | 6 |
| 0.26 | 0.203 | — | — |
| 0.13 | 0.238 | 0.024 | 2 |
| 0.065 | 0.276 | 0.062 | 6 |
| 0 | 0.214 | — | — |

[1] Activity of trypsin control ≈ 1.258. Trypsin concentration = $15.5 \times 10^{-8}$M in incubation mixture.
[2] $T_4$ antibody ≈ $1 \times 10^6$M binding sites in 8.3 mg/ml antibody solution.
[3] Modulation defined as in Table I of Example II.

EXAMPLE IV

The utility of trypsin and soybean-thyroxine conjugate (STI-T4) reagents for assaying for thyroxine is demonstrated as follows:

The following reagents were used:

Thyroxine Standards:
0, 3, 6, 12 and 20 µg% in 0.05 M barbital buffer pH 8.6 containing 0.1% gelatin and 0.25 mg/ml ANS (anilinonaphthalene sulfonic acid). These standards are prepared from 1 mM thyroxine stock solution in 0.5 N sodium hydroxide and 30% propylene glycol.

T4 Antibody:
A working solution of 1 mg/ml anti-T4 IgG (from sheep antiserum) is prepared in barbital buffer with gelatin. The approximate concentration of binding sites from Scratched analysis is $1.2 \times 10^{-7}$ M.

STI-T4 Conjugate:
A working solution of $2.5 \times 10^{-7}$ M STI-T4 in barbital gelatin buffer is prepared from a 46 µM stock solution of the material prepared in Example I.

Trypsin:
A working solution of trypsin at $1.3 \times 10^{-6}$ M is prepared in 2 mM HCl and a 100 µl syringe filled with reagent. The syringe is mounted to a Hamilton repeating dispenser for accurate addition of 2 µl aliquots.

Substrate:
0.5 mM solution of benzoyl phenylalanylvalyl arginine p-nitro anilide in 0.05 M Tris pH 8.1 buffer containing 0.011 M $CaCl_2$.

The specified amounts of reagents are mixed in a tube and incubated for 5 minutes at room temperature: 50 µl STI-T4, 100 µl T4, and 100 µl antibody. The reagents are added in the order listed. Aliquots (50 µl) of the mixture are then sampled and transfered to the sample cup of a bichromatic kinetic analyzer. Trypsin is added to each sample cup for 36 seconds, then a 25 µl portion of the mixture delivered to the bichromatic spectrophotometer cuvette (37° C.) and mixed with 250 µl of substrate. The enzyme rate is printed 5 minutes later. Table III indicates the assay response to increasing concentrations of thyroxine in the physiologic range (2–20 µg% or $0.026 \rightarrow 0.26 \times 10^{-7}$ M). Final concentrations are $5 \times 10^{-8}$ M STI-T4, $1.0 \rightarrow 10.00 \rightarrow 10^{-8}$ M T4, and $5 \times 10^{-8}$ M trypsin.

TABLE III

| µg % Thyroxine | Absorbance at 380 nm |
| --- | --- |
| 0 | 0.60 |
| 3.0 | 0.57 |
| 6.0 | 0.47 |
| 12.0 | 0.40 |
| 20.0 | 0.33 |

EXAMPLE V

N-bromoacetyl-L-thyroxine methyl ester

To a suspension of L-thyroxine methyl ester (Biochem. J., 22 (1978) 1436, (417 mg, 0.473 mmole), in 2 ml of tetrahydrofuran is added bromoacetyl N-hydroxysuccinimide ester (J. Biol. Chem., 252 (1977) 6076, (184 mg, 0.78 mmole). The mixture is stirred for 3 hours at room temperature and then evaporated to a syrup which solidified. The solid is thoroughly washed with water and dried in vacuo to afford 262 mg of product.

The TLC in 10% methanol in methylene chloride showed a single spot, Rf 0.9.

This compound is coupled to soybean trypsin inhibitor at pH 10 and purified substantially by the methods set out in Example I.

EXAMPLE VI

N-acetyl-L-thyroxine
N-(5-carboxypentyl)-carboxamide

N-acetyl-L-thyroxine (Anal. Biochem., 33 (1970) 67) (1.0 g, 1.22 mmole) and N-hydroxysuccinimide (0.148 g, 1.28 mmole) are dissolved in 2 ml of dimethylformamide and 3 ml of tetrahydrofuran. Dicychlohexylcarbodiimide (0.264 g=1.28 mmole) is then added all at once and the reaction mixture stirred at room temperature for 4 hours. The dicyclohexylurea is removed by filtration and to the filtrate is added a solution of 6-aminocaproic acid (160 mg, 1.22 mmole) and sodium bicarbonate (204 mg, 2.44 mmole) in 1 ml of water. After stirring 2 hours the reaction mixture is acidified to pH 3 with 2 N HCl and extracted with methylene chloride. The organic extract is dried over magnesium sulfate and evaporated to the crude amide. Purification of the product is achieved by dissolving the crude material in methylene chloride containing a trace of methanol and precipitating the product with ether/hexane (75:25). The procedure is repeated two times to give 223 mg (23%) of pure product. It shows a single spot on TLC in 8% methanol in chloroform. The compound has the formula $C_{22}H_{24}N_2O_6I_4$ and the following structure

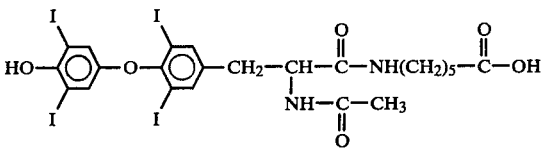

The succinimide ester of this compound is prepared by methods described in Example I and further reacted to provide thyroxine-soybean trypsin inhibitor conjugate.

EXAMPLE VII

Thyroxine concentrations in serum are determined in the following manner. Inferfering serum proteins are removed by precipitation with organic solvents, such as ethanol, butanol and the like or inactivated by heat treatment, disulfide reduction, or other standard methods of protein denaturation. It should be noted that these treatments serve to release thyroxine from its protein carriers in serum, thyroxine binding globulin, pre-albumin, and albumin, as well as remove proteins which interfere with trypsin and the thyroxine-trypsin inhibitor conjugate.

Serum containing varying amounts of thyroxine in the physiologic range ($2.6 \times 10^{-8}$ M to $26 \times 10^{-8}$ M) is treated with 2 N KOH and heated in a water bath for 15 minutes at 60° C. The proportion of serum to base used is 1:1; that is 100 µl serum and 100 µl 2 N KOH. Following inactivation, 50 µl of 8-anilinonaphthalene sulfonic acid (1 mg/ml solution) is added to ensure release of thyroxine from thyroxine binding globulin.

Assay of the serum is then carried out by combining 25 µl of pretreated serum, 25 µl of antibody in 0.25 M HEPES buffer pH 8.0, and 250 µl of thyroxine-soybean trypsin inhibitor conjugate ($2.5 \times 10^{-8}$ M) in 0.04 M citric acid-Tris buffer pH 3.1 at 37° C. for 18 seconds. Trypsin ($1.5 \times 10^{-6}$ M in 0.001 M HCl) is added after 18 seconds and the mixture allowed to incubate for an additional 5 minutes at 37° C. The volume of trypsin added is 3 μl and the concentration of enzyme after dilution in the mixture was $1.5 \times 10^{-8}$ M. The final concentration of thyroxine antibody in the mixture based on binding sites, is approximately $2.3 \times 10^{-8}$ M. At the end of five minutes, 250 μl of substrate (Ortho Diagnostics, benzoyl IleGluGlyArg-p-nitroanilide, $8 \times 10^{-4}$ M in 0.50 M Tris, 0.01 M CaCl$_2$, pH 8.0) is added and the rate of hydrolysis at 37° C. monitored at 380/450 nm for 5 minutes.

EXAMPLE VIII

In a second experiment, serum is pretreated using organic solvent extraction with acetonitrile-H$_2$O mixture (9:1, with 0.5 mg/ml 8-anilino-naphthalene sulfonic acid). The soybean trypsin inhibitor conjugate from Example I is employed.

The following reagents are prepared before carrying out the thyroxine assay.

Combined Trypsin, Thyroxine-soybean Trypsin Inhibitor (T$_4$-STI), Antibody Reagent:

The three main reagents are combined in 0.02 M glycine HCl buffer, pH 3.4 with 0.1% gelatin. The concentrations used are $2.0 \times 10^{-8}$ M trypsin, $4.0 \times 10^{-8}$ M T$_4$-STI, and $3.3 \times 10^{-8}$ M antibody binding sites. Premixing the reagents at ca pH 3.0 reduces the number of manipulation steps in the assay without sacrificing assay performance, since interaction of trypsin and antibody with the thyroxine inhibitor conjugate is minimal at this pH.

Substrate: H-D-phenylalanyl pipercolyl arginine p-nitroanilide (S-2238, from Ortho Diagnostics) was dissolved at $6.7 \times 10^{-4}$ M in 0.05 M Tris 0.01 M CaCl$_2$, pH 8.0 buffer.

Tris Buffer—2 M, pH 10.0: To a series of tubes containing 100 μl aliquots of thyroxine standards in human serum are added 200 μl portions of acetonitrile (90% acetonitrile, 10% aqueous ANS). The mixture is agitated vigorously for 10 seconds, then centrifuged briefly. Portions of the supernatant are transferred to the sample cup of the bichromatic spectrophotometer. The assay is initiated by combining 250 μl of the premixed reagents and 15 μl of Tris buffer with 25 μl of the extracted test sample. The assay mixture is incubated for 5 minutes at 37° C., then 250 μl of substrate added. The results are as follows:

| Thyroxine Conc. in Serum Standards | Final thyroxine Conc. in Assay | 5 Min. Absorbance Change at 380/450nM |
| --- | --- | --- |
| $2.6 \times 10^{-8}$M | $0.74 \times 10^{-9}$M | 1.256 |
| $9.0 \times 10^{-8}$M | $2.4 \times 10^{-9}$M | 1.170 |
| $1.55 \times 10^{-7}$M | $4.4 \times 10^{-9}$M | 1.036 |
| $2.6 \times 10^{-7}$M | $7.4 \times 10^{-9}$M | 1.014 |

The values are conveniently read by constructing a serum standard curve of absorbance vs. μg% thyroxine.

What is claimed is:

1. Hapten-trypsin inhibitor conjugate having 1-3 molecules of hapten per molecule of trypsin inhibitor wherein the trypsin inhibitor is a protein trypsin inhibitor having a molecular weight range of 2,000–75,000.

2. Thyroxine-trypsin inhibitor conjugate having 1-3 molecules of thyroxine per molecule of trypsin inhibitor wherein the trypsin inhibitor is a protein trypsin inhibitor having a molecular weight range of 2,000–75,000.

* * * * *